US00PP08688P

United States Patent [19]

Austin

[11] Patent Number: Plant 8,688

[45] Date of Patent: Apr. 19, 1994

[54] ROSE PLANT 'AUSGOLD'

[75] Inventor: David C. H. Austin, Wolverhampton, England

[73] Assignee: David Austin Roses Limited, Albrighton, England

[21] Appl. No.: 954,964

[22] Filed: Sep. 30, 1992

[51] Int. Cl.[5] ..... A01H 5/00

[52] U.S. Cl. ..... Plt./1

[58] Field of Search ..... Plt. 1, 24

*Primary Examiner*—Howard J. Locker
*Assistant Examiner*—E. F. McElwain
*Attorney, Agent, or Firm*—Klarquist, Sparkman, Campbell, Leigh & Whinston

[57] ABSTRACT

A shrub rose variety having large flowers, bushy plant, and distinctive yellow flowers.

1 Drawing Sheet

The present invention relates to a new and distinct variety of shrub rose plant of the *Rosa hybrida* class which was originated by me by crossing the variety Charles Austin, with the variety Abraham Darby.

The primary objective of this breeding was to produce a new shrub rose variety having yellow, quartered, scented flower on a bushy plant which repeatedly flowers. The objective was substantially achieved along with other desirable improvements as evidenced by the following unique combination of characteristics which are outstanding in the new variety and which distinguish it from its parents, as well as from all other varieties of which I am aware:

1. Large flowers,
2. Bushy plant; and
3. Distinctive yellow flowers.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated. In one instance, color is noted in accordance with the R.H.S. Colour Chart of The Royal Horticultural Society, London, England.

Parentage:

*Seed parent.*—Charles Austin.

*Pollen parent.*—Abraham Darby.

Classification:

*Botanical.*—*Rosa hybrida.*

*Commercial.*—Shrub.

FLOWER

Observations made from specimens grown in a garden environment in Albrighton, Wolverhampton, England, in August 1991.

Blooming habit: Recurrent.

Bud:

*Size.*—About ¾-1¼" long when the petals start to unfurl.

*Form.*—The bud form is short, globular with cuspidate apex.

*Color.*—When sepals first divide, the bud color is light yellow 1A5 to greyish yellow 1B5 with violet brown blush 11E8. The outer surface of the outer petals of the bud has a relatively large patch of R.H.S. color red 47A, which fades to a light pink blush as the flower opens. When half blown, the upper and lower sides of the petals are pastel yellow 3A4 with a very light pink blush 9A2 at top edge of petal changing to light yellow 3A5 at the center.

*Sepals.*—Color: Green 29E7. Surface texture: Leathery and slightly ridged. There are three normally appendaged sepals. There are two unappendaged sepals with hairy edges.

*Receptacle.*—Color: Deep green 29E8. Shape: Goblet shaped. Size: Medium, about ½"×5/16". Surface: Smooth.

*Peduncle.*—Length: Medium, averaging about 1-1¾". Surface: Slightly glandular. Color: Light green, bronzy, greyish yellow 2B5 with reddish brown blush 9D5. Strength: Stiff, erect.

Bloom:

*Size.*—Medium. Average open size is 2½-2¾" in diameter.

*Borne.*—Singly, several together, the clusters of up to 8 flowers having irregular shape.

*Stems.*—Average length in 18 to 30 inches.

*Form.*—When first open: Globular. Permanence: Flattens slightly, outer petal edges curl slightly.

*Petalage.*—Number of petals under normal conditions: 55 to 75.

*Color.*—The upper side of the petals is pastel yellow 3A4 (top edge of petal changing to light yellow 3A5 towards the center of the petal). The reverse side of the petals is same as above except for a very slight pink blush. The color of the base of the petals is yellow 3A6 at the apex. The major color on the upper side is light yellow 3A5.

*Variegations.*—None.

*Height.*—42 to 48".

*Discoloration.*—The general tonality at the end of the first day: Slightly paler. At the end of the third day, the majority of petals are pastel yellow 3A4 at the top edge changing to light yellow 3A5 towards the center of the petal.

*Fragrance.*—Strong and sweet.

Petals:

*Texture.*—Thin, soft and silky.

*Shape.*—Deltoid, round, cupped, apex retuse.

*Form.*—Tips slightly recurved.

*Arrangement.*—Slightly quartered with few petaloids in the center.

*Persistence.*—Petals drop off cleanly before drying.

*Lastingness.*—On the plant: About 7 to 10 days. As a cut flower: 5 to 7 days.

Reproductive parts:

*Anthers.*—Size: Medium. Quantity: Many (95 to 115). Color: Vivid yellow 3A8 to deep yellow 4A8. Arrangement: Tucked in calyx or partly so, mixed with petaloids.

*Filaments.*—Color: Light yellow 3A5.

*Pollen.*—Color: Gold yellow.

*Styles.*—Color: Pale green 30A3.

*Stigmas.*—Color: Light yellow 3A5.

Form: Shrub.

Growth: Medium, branching.

Foliage:

*Number of leaflets on normal mid-stem leaves.*—7.

*Size.*—Large, about 1½"-2½" long × 1¼"-2" wide.

*Quantity.*—Normal.

*Color.*—New foliage: Deep green 28E8 to dark green 28F8. Old foliage: Dark green 28F8.

Leaflets:

*Shape.*—Oval, cuspidate apex, rounded base.

*Texture.*—Upper side: Leathery.

*Edge.*—Serrated.

*Serration.*—Double, medium.

*Petiole rachis.*—Color: Green, reddish. Parrot green 30E8 tinged with violet brown 11D7.

*Petiole underside.*—With prickles, 0 to 2 per internode and sparse glandular hairs.

*Stipules.*—Medium, serrated, about 1¼" long.

*Disease resistance.*—Resistant to mildew and blackspot under normal growing conditions at Albrighton, Wolverhampton, England.

Wood:

*New Wood.*—Color: Parrot green 30E8, violet brown blush 10E7. Bark: Smooth.

*Old wood.*—Color: Deep green 28E8. Bark: Smooth.

Prickles:

*Quantity.*—On main canes from base: Ordinary: On laterals from main canes: Ordinary:

*Form.*—Medium, hooked downward.

*Color when young.*—Green and red. Brownish red 10C7. at the base fading to greyish yellow 1B4 at the tip.

*Position.*—Evenly distributed.

Small prickles:

*Quantity.*—On main stalks: None. On laterals: None.

I claim:

1. A new and distinct variety of shrub rose plant of the *Rosa hybrida* class, substantially as herein shown and described, characterized particularly as to novelty by the unique combination of its large flowers, bushy plant, and distinctive yellow flowers.

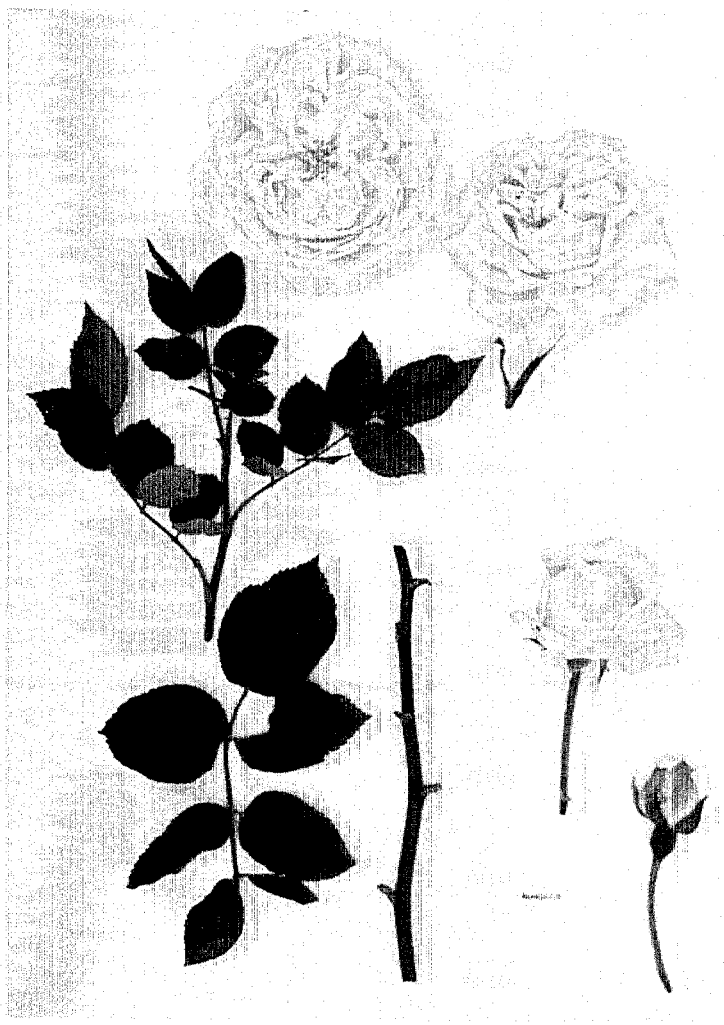

* * * * *